United States Patent [19]

Couvillon, Jr. et al.

[11] 4,089,329
[45] May 16, 1978

[54] NONINVASIVE, CONTINUOUS INTRAOCULAR PRESSURE MONITOR

[75] Inventors: Lucien Alfred Couvillon, Jr., Salt Lake City, Utah; Thomas Reaks Grover, San Francisco, Calif.; Charles Dewitt Baker, Salt Lake City, Utah; William Sanford Topham, Chagrin Falls, Ohio

[73] Assignee: University of Utah Research Institute, Salt Lake City, Utah

[21] Appl. No.: 668,020

[22] Filed: Mar. 18, 1976

[51] Int. Cl.² .............................................. A61B 3/16
[52] U.S. Cl. ...................................... 128/2 T; 73/80; 128/2.1 A
[58] Field of Search ............... 128/2 T, 2.05 E, 2.1 A; 73/80

[56] References Cited

U.S. PATENT DOCUMENTS

| 3,769,961 | 11/1973 | Fatt et al. | 128/2 T |
| 3,893,444 | 7/1975 | Fatt | 128/2 T X |
| 3,958,560 | 5/1976 | March | 128/2 T X |

OTHER PUBLICATIONS

Investigative Opthalmology, 13:299, Apr. 1974.
Collins, C. C., I.E.E.E. Trans. on Bio.-Med. Engng, Vol. BME-14, No. 2, Apr. 1967, pp. 74–83.
RCA Technical Notes, RCA-TN, No. 602, Dec. 1964, pp. 1-2.

*Primary Examiner*—Kyle L. Howell
*Attorney, Agent, or Firm*—Criddle, Thorpe & Western

[57] ABSTRACT

A noninvasive, continuous monitoring device for measuring intraocular pressure without interference with vision or normal activity of the patient. A miniature, planar-faced pressure transducer is fixed in a protruding section of a compliant hydrogel ring which has been tooled to conform to the spherical surface of the sclera. The hydrogel ring is placed noninvasively under the eyelids within the conjunctival cul-de-sac, the transducer being located in the lower temperal quadrant. Applanation of the sclera against the planar surface of the transducer results as a consequence of pressure from the separated tissues. Intraocular pressure readings are based on the variations in resistance in the strain gage elements of the transducer caused by the applied stress to the transducer diaphragm. Data is transmitted through connecting wires to a telemetry unit which transmits the data to a receiver-transcriber console. The total system permits free, uninhibited movement by the patient during the monitoring process and provides a record of intraocular pressure as a function of time-of-day.

11 Claims, 2 Drawing Figures

NONINVASIVE, CONTINUOUS INTRAOCULAR PRESSURE MONITOR

The invention described herein was made in the course of work under a grant or award from the Department of Health, Education, and Welfare.

BACKGROUND

1. Field of the Invention

This invention relates to an improved tonometric measuring device for detecting excessive intraocular pressure such as that associated with glaucoma.

2. Prior Art

The current diagnosis of glaucoma relies on the detection of increased intraocular pressure. Numerous methods for making such measurements have been utilized, including both invasive and non-invasive techniques. The primary non-invasive instruments have generally involved a tonometric measurement over the cornea, resulting in discomfort to the patient and incapacitation during the period of measurement. Where the measurement is made by appanation of a small surface area, the contacting diaphragm is usually of a compliant form, as opposed to being essentially noncompliant. The use of the compliant form in connection with the pressure applied results in a gradual decrease in IOP due to forced fluid escape during the measurement process. Such fluid escape attenuates accuracy in continuous monitoring methods due to the cumulative loss of fluid pressure. Furthermore, the variation of intraocular pressures occurring over an extended period of time or with change in activity makes isolated measurements less informative as to the true condition of the patient. For example, a patient may have a moderately high pressure reading while in a prone or restful position, but experience more dangerous pressure levels when involved in exhilarating or emotional activities.

Most current instrumentation is not adaptable to continuous measurement because a technical assistant is required to be present or the vision of the patient is impaired, thereby restricting activity or movement. A detailed discussion of the prior art relating to noninvasive measurement of IOP is found in Macri and Brubaker, "Methodology of Eye Pressure Measurement," *Biorheology* 6.37, 1969.

The continuous measurement of intraocular pressure over longer periods of time is more closely comprehended by a contact lens measuring device which is worn over the cornea in a manner similar to normal contact lenses. This device is described in Green and Gilman, "Intraocular Pressure Measurement with Instrumented Contact Lenses," *Investigative Ophthalmology*, 13:299, April, 1974. Essentially, it comprises a flush-fitting silastic gel contact lens implanted with strain gauges for measuring changes in the meridional angle of the corneoscleral junction. This application of tonometric measurement relies on the theoretically predicted angular change of 0.020 to 0.016 radians per mm Hg change of intraocular pressure.

The use of the contact lens material permits the patient to enjoy unobstructed vision during measurement; however, the sensitivity of the cornea results in limitations to continuous use caused by eye irritation and inflamation similar to that experienced with the prolonged wearing of regular contact lenses. Furthermore, the measurement of intraocular pressure with reference to the corneoscleral junction requires an in situ calibration which may cause some discomfort and inconvenience to the patient.

What is needed, therefore, is a device for continuously measuring intraocular pressure over an extended period of time without causing irritation to the eye or requiring special in situ calibration techniques, while retaining the requisite noninterfering characteristics which permit the patient to engage in his normal activity.

BRIEF SUMMARY AND OBJECTIVES OF THE INVENTION

Intraocular pressure is monitored by means of a miniature strain gauge pressure transducer which has an essentially noncompliant, planar diaphragm for applanating a small portion of the sclera. The transducer is mounted in a protruding section of a hydrogel ring, the total structure conforming to the spherical shape of the eye. The ring is placed within the conjunctival cul-de-sac of the eye in a concentric orientation with the cornea, thereby preserving the normal vision of the patient during the monitoring process. The protruding section with the attached transducer fits conveniently into the extended portion of the conjunctival cul-de-sac region in the lower temporal quadrant. Other areas may be similarly adapted to transducer placement.

The separation of tissue supplies the necessary force to the transducer diaphragm to applanate the contacted portion of the sclera. The resultant stress applied to the strain gauges of the transducer is monitored as variations in resistance and is communicated to a small transmitter through connecting wires. The data is telemetered to a receiver-transcriber console which records the intraocular pressure as a function of time of day.

It is an object of the present invention to provide a non-invasive device for continuously monitoring intraocular pressure in a patient without limiting vision or restricting activity.

It is a further object of the present invention to provide a tonometric device for continuously measuring intraocular pressure by applanating a small portion of the sclera.

It is a still further object of this invention to provide a holding device for instrumentation which requires stable positioning in association with the ocular environment.

DETAILED DESCRIPTION OF THE INVENTION

Figure 1:
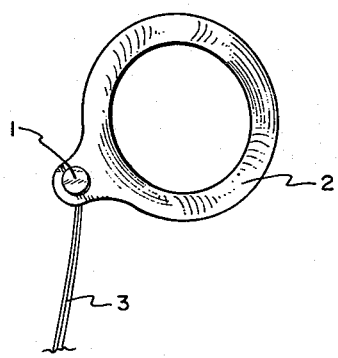
FIG. 1 depicts the hydrogel ring and attached transducer viewed from the patient's perspective immediately prior to placement over the eye.

This invention involves the tonometric measurement of intraocular pressure by applanation of a small portion of the sclera. The resultant pressure is monitored by means of a strain gauge pressure transducer. The shifting of the tonometric device from the cornea to the sclera provides several advantages over the prior art. Since the scleral surface of the eye is more insensitive to irritation and inflamation than the corneal tissue, the scleral contact with the foreign device does not result in serious discomfort, even after prolonged use. The location of the tonometric device on the sclera also avoids obstruction of vision previously associated with corneal measurement.

The complete system for monitoring intraocular pressure comprises four elements:

(1) a transducer or other pressure sensing instrument which operates on the surface of the sclera in a non-invasive manner and is responsive to the variations of pressure evidenced by the tension at the scleral surface;
(2) a holding member which retains the transducer in suitable orientation in the ocular environment without causing undue irritation to tissue or interference with ocular functions;
(3) a means for communicating the pressure readings to a receiver-transcriber; and
(4) a receiver-transcriber which analyzes the data and records the information in an appropriate form.

These elements are categorically discussed in detail as follows.

1. Transducer

Numerous types of pressure sensitive transducers are available in the state of the art which could be engineered to the miniature size and stability required for monitoring intraocular pressure at the scleral surface. One specific embodiment comprises a planar-faced, strain gauge pressue transducer 1 designed by Konigsberg Instruments, Inc. of Pasadena, Cal. In this embodiment, the transducer case is made of stainless steel, Ti-6A1-4V or unalloyed titanium. A planar-faced diaphragm of 2.5 to 3.0 mils thickness is made from titanium and has a maximum deflection of 0.5 micron at 50mm Hg at the center of the diaphragm face. This essentially noncompliant diaphragm permits continuous monitoring for extended periods without the previously noted decrease in IOP due to forced fluid escape. The casing is bonded or welded for water tight construction and has dimensions of approximately 5.00mm across the diameter of the diaphragm and 2.50mm maximum height.

Two strain gauges are mounted within the transducer, responsive to varying degrees of diaphram displacement. A centrally located gauge provides the primary pressure reading while a second gauge located at the edge of the transducer constitutes the means for compensating for variations in temperature. This coordination of two strain gauges provides for zero drift during monitoring procedures. To accomplish the necessary miniaturization, strain gauges of 5000 ohms were utilized.

Conducting wires 3 enter the transducer through a water-tight lateral opening on the cap end of the transducer casing and provide current for the strain gauge elements. A silicone rubber coating renders the exposed wires compatible with body tissue.

2. Transducer Holder

Figure 2:
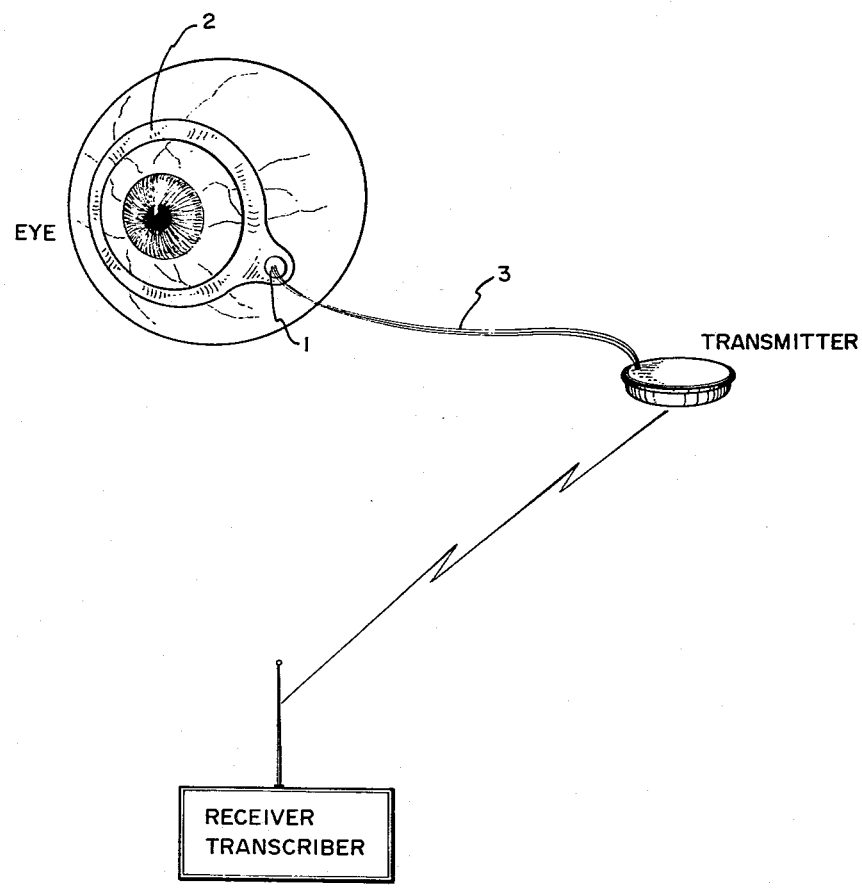
FIG. 2 represents a potential position of the ring on the sclera, in combination with the transmitter unit and receiving console.

The transducer is retained in the desired position on the sclera (FIG. 2) by means of a contoured, stable, ring platform 2 having a protruding section for holding the transducer. When the ring is in a concentric orientation with the cornea, the contoured section fits conveniently into the conjunctival cul-de-sac region. To prevent corneal irritation, the corneal opening bounded by the ring plateform 2 must be approximately 2cm in diameter. This size opening is sufficient to allow eye movement without serious contact with corneal tissue.

The holder material must be compatible with the body tissue and of sufficient compliance to respond to ocular movements without being dislodged or causing irritation. Furthermore the material must have physical properties which permit structural fabrication which conforms to the spherical surface of the sclera.

One class of materials which complies with the above considerations is the general class of body compatible polymers. Specifically, hydrophilic plastics such as that used as contact lens material can be tooled to the appropriate structure prior to water absorption and then hydrated to a compliant form. Of the various hydrogel or hydrophilic plastics, "poly-hema" (polyhydroxyethylmethacrylate) has been successfully utilized as holder material.

The specific procedure for constructing the hydrogel holder begins with obtaining a large blank of "poly-hema" material. This material is commercially available and may be obtained in suitable blanks of 3.5 cm diameter X 2.5 cm. Machining techniques are similar to those used for processing polymethyl methacrylate; however, since the "poly-hema" material tends to chip more readily, care must be taken to select the proper cutting tool and feed speed.

An appropriate blank of material is machined and hollowed to an inner spherical radius of ½ inch, approximating the curvature of the eye. A hole is then drilled in the center of the blank and the material is fastened by means of a screw to a fixture having a matching spherical head for receiving the hollowed portion of the blank. The outer surface of the blank is then tooled to the desired thickness, such that the blank is now in the form of a spherical cup. The proper holder shape is then drawn on the outer surface of the blank and the excess material is cut away using a carbide deburring tool attached to a flexible shaft drive.

The thickness for the ring is a function of the size of the cul-de-sac receptacle and the natural resilience of the separated tissue (eye lid). For proper applanation the threshold pressure required for accurate transducer response under the Imbert-Fick law must be applied by the resilience of the stretched tissue of the eye lid and conjunctiva. For older persons this thickness will normally be larger since the tissue tends to be somewhat limp. Such adjustments may usually be made to the thickness of the protruding section without the need to thicken the full ring structure and thereby create excessive bulk which might inhibit normal ocular movement. A suitable prehydration ring thickness is approximately 0.5mm to 3mm, with the peripheral edges tapered.

The roughed-out form of the holder is finished by hand, cutting and shaping to the desired structure with a Swiss file and wet-dry sandpaper. Final polishing is completed by using a small multi-layer cloth wheel without rouge, since polishing heat must be minimized to avoid melting the material. Because nonhydrated material will expand with the absorption of water, the thickness of the tooled holder must be reduced by an appropriate expansion factor "poly-hema" expands in a linear dimension by about 30%; therefore, a corresponding decrease in thickness must be provided.

The receptacle for the transducer is milled in the inner surface of the protruding section of the ring, making a similar allowance for hydration expansion. The final receptacle dimensions should enable the transducer to be retained by friction, with a suitable path provided for the conducting wires to exit the receptacle cavity.

Once the edges have been contoured and the material hydrated to achieve the necessary compliance, the holder is ready for emplacement under the eye lids of the patient. A preferred location for the protruding section of the ring is in the lower temporal quadrant of the conjunctival cul-de-sac due to the less active movement of the lower eye lid and the more spacious area for holding the transducer. When the holder has been properly emplaced, it will remain in position without being rotated or dislodged by normal eye movement.

3. Communicating Means From Transducers

The figures illustrate the use of wire conductors to convey the current to operate the transducer. Variations in the resistance of the strain gauges are measured as changes in voltage which provide the intelligence for determination of IOP. Such voltage variations are conveyed through the connecting wires to a small transmitter which may be fixed to the patient's glasses or person. The necessary transducer current is supplied by a small battery-pack within the transmitter.

To preserve battery power, a timing circuit is included in series with the battery pack such that the circuit is only closed for 1 minute out of every 10 minute period. The remaining circuitry includes a voltage-to-frequency converter which develops a pulse train output whose frequency is approximately linearly related to the pressure transducer signal. RF circuits provide the means for transmitting the intelligence to a receiving console.

Although the disclosed system utilizes conducting wires, it will be apparent to one skilled in the art that the RF circuits of the transmitter could be reduced in size for inclusion within a modified transducer. Power could be supplied inductively to the transducer from an external source, and the connecting wires could thus be eliminated. Other methods of power-signal coupling could be substituted to pass intelligence from a transducer to an external transmitting unit, for relay to the receiver console.

4. Receiver - Transcriber Console

Any compatible receiving unit may be utilized for receiving the transmitted intelligence. A suggested embodiment of the console would include the following functions;
(a) generating codes for time of day and barometric pressure;
(b) receiving and demodulating transmitter pulses;
(c) recording the corresponding transmitter pulses with the time of day and barometric pressure data; and
(d) visually displaying the pressue read-out, time of day and barometric pressure functions.

Operating as a system, the noninvasive, continuous intraocular pressure monitor allows the patient to pursue normal activities without discomfort or restriction. Periodic transmissions will be recorded for evaluation of the IOP as a function of time of day over the full 24 hour period. This data can then be utilized to diagnose the extent of glaucoma and to give notice of dangerously high IOP.

We claim:

1. A noninvasive monitoring device for measuring intraocular pressure, comprising
   a. pressure transducer means adapted to contact and applanate a portion of a scleral surface for responsive detection of intraocular pressure changes reflected at said scleral surface, and
   b. holder means operable to position and independently retain the transducer means in said scleral contact, said holder being made of materials chemically and mechanically compatible with an ocular environment.

2. A device as defined in claim 1, further comprising means operable to transmit pressure data detected by said transducer means to a receiving means.

3. A device as defined in claim 1, wherein said holder means comprises an annular member having inner concave and outer convex spherical surfaces and an annulus opening, the combination being adapted for emplacement around a corneal region and in contact with a surrounding scleral region of an eye.

4. A device as defined in claim 3 wherein said inner concave surface is conformed to and adapted for emplacement on a selected scleral surface.

5. A device as defined in Claim 1, wherein the holder material is selected from the group consisting of tissue compatable, hydrophilic polymers.

6. A device as defined in claim 5, wherein the material is polyhydroxyethylmethacrylate.

7. A device as defined in claim 2, further comprising a telemetry means in combination with said receiving means for wireless transmission of said data to a receiving/recording means.

8. A device as defined in claim 3, wherein said annular member further comprises a protruding section extending away from said annulus opening, said section having positioning means for retaining said transducer means therein in contacting relationship with said scleral surface.

9. A noninvasive monitoring device for measuring intraocular pressure, comprising:
   a. a noninvasive, pressure sensitive instrument having a contacting face and responsive means for detecting surface characteristics of a scleral region wherein said characteristics are indicative of intraocular pressure conditions,
   b. an annular holding member having inner concave and outer convex spherical surfaces and an annulus opening of sufficient diameter such that the holding member, when positioned in scleral contact within an ocular environment wherein said annulus opening is axially aligned with a corneal region, circumscribes said corneal region in substantial noncontacting relationship thereto, said holding member further including a positioning receptacle for receiving said pressure sensitive instrument and positioning the contacting face thereof at a surface of said scleral region, whereby said contact is adapted to be maintained by tissue separation forces exerted by stretched eyelid tissue distended as a result of insertion of said monitoring device thereunder.

10. A method for noninvasive monitoring of intraocular pressure comprising the steps of:
    a. affixing a noninvasive, pressure sensitive instrument to an annular holding means having an annulus opening of a diameter greater than a corneal region diameter;
    b. inserting said annular holding means between an eyelid and a portion of scleral surface covered by said eyelid, said instrument being positioned in direct contact with a portion of scleral surface of said eye and having said opening substantially concentric with said corneal region to provide unobstructed view during monitoring procedures; and c. detecting changes in intraocular pressure as refected by changes of physical property data registered by said pressure sensitive instrument at said scleral contact therewith.

11. A method as defined in claim 9, further comprising the step of transmitting said physical property data to a receiver for data processing.

* * * * *